(12) United States Patent
Wolf et al.

(10) Patent No.: US 6,641,610 B2
(45) Date of Patent: *Nov. 4, 2003

(54) VALVE DESIGNS FOR LEFT VENTRICULAR CONDUITS

(75) Inventors: Scott J. Wolf, Minneapolis, MN (US); Greg R. Furnish, Louisville, KY (US); Todd A. Hall, Goshen, KY (US); David Y. Phelps, Louisville, KY (US); Peter J. Wilk, New York, NY (US); Nancy C. Briefs, Nashua, NH (US); William Santamore, Medford, NJ (US); Daniel Burkhoff, Tenafly, NJ (US)

(73) Assignee: Percardia, Inc., Nashua, NH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/368,393

(22) Filed: Aug. 4, 1999

(65) Prior Publication Data

US 2002/0165606 A1 Nov. 7, 2002

Related U.S. Application Data

(60) Provisional application No. 60/099,777, filed on Sep. 10, 1998.

(51) Int. Cl.[7] ............................. A61F 2/06; A61B 17/08
(52) U.S. Cl. ........................................ 623/1.3; 606/153
(58) Field of Search ............................... 623/2.35, 1.11, 623/1.12, 1.36, 1.42, 1.43, 1.44, 1.46; 128/898; 600/16, 17, 18; 606/153, 191, 192, 194, 198, 151, 152; 604/8, 9

(56) References Cited

U.S. PATENT DOCUMENTS

| | | | |
|---|---|---|---|
| 3,671,979 A | 6/1972 | Moulopoulos |
| 3,858,246 A | 1/1975 | Milo |
| 3,911,502 A | 10/1975 | Boretos |
| 3,926,215 A | 12/1975 | Macleod |
| 4,441,215 A | 4/1984 | Kaster |

(List continued on next page.)

FOREIGN PATENT DOCUMENTS

| | | |
|---|---|---|
| EP | 0 732 088 | 9/1996 |
| EP | 0 824 903 | 2/1998 |

(List continued on next page.)

OTHER PUBLICATIONS

US 6,331,185, 12/2001, Gambale et al. (withdrawn)
*American Medical Association Publication*; International Cardiovascular Society, "Myocardial Boring for the Ischemic Heart," A. Wakabayashi, M.D., et al.; Fifteenth Scientific Meeting, Atlantic City, NJ, Jun. 16 and 17, 1967; *Archives of Surgery*, pp. 743–752, vol. 95, No. 5, Nov. 1967.

(List continued on next page.)

*Primary Examiner*—David J. Isabella
(74) *Attorney, Agent, or Firm*—Finnegan, Henderson, Farabow, Garrett & Dunner, LLP

(57) ABSTRACT

Disclosed is a conduit that provides a bypass around a stenosis or occlusion in a coronary artery. The conduit is adapted to be positioned in the myocardium to provide a passage for blood to flow from a heart chamber to a coronary artery, at a site distal to the blockage or stenosis in the coronary artery. The conduit has a one-way valve positioned therein to prevent the backflow of blood from the coronary artery into the heart chamber.

32 Claims, 8 Drawing Sheets

U.S. PATENT DOCUMENTS

| | | | |
|---|---|---|---|
| 4,503,568 A | | 3/1985 | Madras |
| 4,655,773 A | | 4/1987 | Grassi |
| 4,680,031 A | * | 7/1987 | Alonso ................. 623/2.13 |
| 4,733,665 A | | 3/1988 | Palmaz |
| 4,769,029 A | | 9/1988 | Patel |
| 4,979,955 A | | 12/1990 | Smith |
| 4,995,857 A | | 2/1991 | Arnold |
| 5,035,702 A | | 7/1991 | Taherei |
| 5,135,467 A | | 8/1992 | Citron |
| 5,193,546 A | | 3/1993 | Shaknovich |
| 5,258,008 A | | 11/1993 | Wilk |
| 5,287,861 A | | 2/1994 | Wilk |
| 5,330,486 A | | 7/1994 | Wilk |
| 5,332,402 A | * | 7/1994 | Teitelbaum ............ 623/2.35 |
| 5,344,426 A | | 9/1994 | Lau et al. |
| 5,385,541 A | | 1/1995 | Kirsch et al. |
| 5,397,351 A | * | 3/1995 | Pavcnik ................. 623/2.35 |
| 5,409,019 A | | 4/1995 | Wilk |
| 5,423,744 A | | 6/1995 | Gencheff et al. |
| 5,423,851 A | | 6/1995 | Samuels |
| 5,429,144 A | * | 7/1995 | Wilk ........................ 128/898 |
| 5,443,497 A | | 8/1995 | Venbrux |
| 5,456,712 A | | 10/1995 | Maginot |
| 5,456,714 A | | 10/1995 | Owen |
| 5,470,320 A | | 11/1995 | Tiefenbrun et al. |
| 5,487,760 A | | 1/1996 | Villafana |
| 5,500,014 A | | 3/1996 | Quijano et al. |
| 5,527,337 A | | 6/1996 | Stack et al. |
| 5,554,185 A | * | 9/1996 | Block et al. ............. 623/2.12 |
| 5,571,215 A | | 11/1996 | Sterman et al. |
| 5,578,075 A | | 11/1996 | Dayton |
| 5,593,434 A | | 1/1997 | Williams |
| 5,609,626 A | | 3/1997 | Quijano et al. |
| 5,618,299 A | | 4/1997 | Khosravi et al. |
| 5,655,548 A | * | 8/1997 | Nelson et al. ........... 128/898 |
| 5,662,124 A | | 9/1997 | Wilk |
| 5,713,950 A | | 2/1998 | Cox |
| 5,755,682 A | | 5/1998 | Knudson et al. |
| 5,758,663 A | | 6/1998 | Wilk et al. |
| 5,797,933 A | | 8/1998 | Snow et al. |
| 5,810,836 A | | 9/1998 | Hussein et al. |
| 5,824,038 A | | 10/1998 | Wall |
| 5,824,071 A | | 10/1998 | Nelson et al. |
| 5,830,222 A | | 11/1998 | Makower |
| 5,843,163 A | | 12/1998 | Wall |
| 5,851,232 A | | 12/1998 | Lois |
| 5,855,597 A | | 1/1999 | Jayaraman |
| 5,865,723 A | | 2/1999 | Love |
| 5,876,419 A | | 3/1999 | Carpenter et al. |
| 5,878,751 A | | 3/1999 | Hussein et al. |
| 5,908,028 A | | 6/1999 | Wilk |
| 5,908,029 A | | 6/1999 | Knudson et al. |
| 5,931,868 A | * | 8/1999 | Gross ........................ 128/898 |
| 5,935,119 A | | 8/1999 | Guy et al. |
| 5,935,161 A | | 8/1999 | Robinson et al. |
| 5,935,162 A | | 8/1999 | Dang |
| 5,944,019 A | | 8/1999 | Knudson et al. |
| 5,961,548 A | | 10/1999 | Shmulewitz |
| 5,968,093 A | | 10/1999 | Kranz |
| 5,971,993 A | | 10/1999 | Hussein et al. |
| 5,976,159 A | | 11/1999 | Bolduc et al. |
| 5,976,169 A | | 11/1999 | Imran |
| 5,976,181 A | | 11/1999 | Whelan et al. |
| 5,976,182 A | | 11/1999 | Cox |
| 5,976,192 A | | 11/1999 | McIntyre et al. |
| 5,976,650 A | | 11/1999 | Campbell et al. |
| 5,979,455 A | | 11/1999 | Maginot |
| 5,980,548 A | | 11/1999 | Evans et al. |
| 5,980,551 A | | 11/1999 | Summers et al. |
| 5,980,552 A | | 11/1999 | Pinchasik et al. |
| 5,980,553 A | | 11/1999 | Gray et al. |
| 5,980,566 A | | 11/1999 | Alt et al. |
| 5,980,570 A | | 11/1999 | Simpson |
| 5,984,955 A | | 11/1999 | Wisselink |
| 5,984,956 A | | 11/1999 | Tweden et al. |
| 5,984,963 A | | 11/1999 | Ryan et al. |
| 5,984,965 A | | 11/1999 | Knapp et al. |
| 5,989,207 A | | 11/1999 | Hughes |
| 5,989,287 A | | 11/1999 | Yang et al. |
| 5,993,481 A | | 11/1999 | Marcade et al. |
| 5,993,482 A | | 11/1999 | Chuter |
| 5,997,563 A | | 12/1999 | Kretiers |
| 5,997,573 A | | 12/1999 | Quijano et al. |
| 6,001,123 A | | 12/1999 | Lau |
| 6,004,261 A | | 12/1999 | Sinofsky et al. |
| 6,004,347 A | | 12/1999 | McNamara et al. |
| 6,004,348 A | | 12/1999 | Banas et al. |
| 6,007,575 A | | 12/1999 | Samuels |
| 6,007,576 A | | 12/1999 | McClellan |
| 6,010,530 A | | 1/2000 | Goicoechea |
| 6,017,365 A | | 1/2000 | Van Oepen |
| 6,029,672 A | | 2/2000 | Vanney et al. |
| 6,033,582 A | | 3/2000 | Lee et al. |
| 6,045,565 A | | 4/2000 | Ellis et al. |
| 6,053,911 A | | 4/2000 | Ryan et al. |
| 6,053,924 A | | 4/2000 | Hussein |
| 6,053,942 A | | 4/2000 | Eno et al. |
| 6,067,988 A | | 5/2000 | Mueller |
| 6,068,638 A | | 5/2000 | Makower |
| 6,071,292 A | | 6/2000 | Makower et al. |
| 6,076,529 A | | 6/2000 | Vanney et al. |
| 6,080,163 A | | 6/2000 | Hussein et al. |
| 6,093,166 A | | 7/2000 | Knudson et al. |
| 6,095,997 A | | 8/2000 | French et al. |
| 6,102,941 A | | 8/2000 | Tweden et al. |
| 6,106,538 A | | 8/2000 | Shiber |
| 6,110,201 A | | 8/2000 | Quijano et al. |
| 6,113,630 A | | 9/2000 | Vanney et al. |
| 6,113,823 A | | 9/2000 | Eno |
| 6,117,165 A | | 9/2000 | Becker |
| 6,123,682 A | | 9/2000 | Knudson et al. |
| 6,126,649 A | | 10/2000 | VanTassel et al. |
| 6,139,541 A | | 10/2000 | Vanney et al. |
| 6,152,141 A | | 11/2000 | Stevens et al. |
| 6,159,225 A | | 12/2000 | Makower |
| 6,162,245 A | | 12/2000 | Jayaraman |
| 6,182,668 B1 | | 2/2001 | Tweden et al. |
| 6,186,972 B1 | | 2/2001 | Nelson et al. |
| 6,187,034 B1 | | 2/2001 | Frantzen |
| 6,190,353 B1 | | 2/2001 | Makower et al. |
| 6,193,726 B1 | | 2/2001 | Vanney |
| D438,618 S | | 3/2001 | Solem |
| 6,196,230 B1 | | 3/2001 | Hall et al. |
| 6,197,050 B1 | | 3/2001 | Eno et al. |
| 6,203,556 B1 | | 3/2001 | Evans et al. |
| 6,214,041 B1 | | 4/2001 | Tweden et al. |
| 6,223,752 B1 | | 5/2001 | Vanney et al. |
| 6,231,587 B1 | | 5/2001 | Makower |
| 6,237,607 B1 | | 5/2001 | Vanney et al. |
| 6,238,406 B1 | | 5/2001 | Ellis et al. |
| 6,245,102 B1 | | 6/2001 | Jayaraman |
| 6,250,305 B1 | | 6/2001 | Tweden |
| 6,253,768 B1 | | 7/2001 | Wilk |
| 6,254,564 B1 | | 7/2001 | Wilk et al. |
| 6,258,119 B1 | | 7/2001 | Hussein et al. |
| 6,261,304 B1 | | 7/2001 | Hall et al. |
| 6,283,951 B1 | | 9/2001 | Flaherty et al. |
| 6,283,983 B1 | | 9/2001 | Makower et al. |
| 6,287,317 B1 | | 9/2001 | Makower et al. |
| 6,290,719 B1 | | 9/2001 | Garberoglio |
| 6,290,728 B1 | | 9/2001 | Phelps et al. |

| | | | | | |
|---|---|---|---|---|---|
| 6,293,955 B1 | 9/2001 | Houser et al. | EP | 0 903 123 | 3/1999 |
| 6,302,875 B1 | 10/2001 | Makower et al. | EP | 0 904 745 | 3/1999 |
| 6,302,892 B1 | 10/2001 | Wilk | EP | 0 955 017 | 11/1999 |
| 6,306,125 B1 | 10/2001 | Parker et al. | EP | 0 955 019 | 11/1999 |
| 6,330,884 B1 | 12/2001 | Kim | EP | 0 962 194 | 12/1999 |
| 6,350,248 B1 | 2/2002 | Knudson et al. | EP | 1 020 166 | 7/2000 |
| 6,361,519 B1 | 3/2002 | Knudson et al. | EP | 1 027 870 | 8/2000 |
| 6,363,938 B2 | 4/2002 | Saadat et al. | EP | 1 097 676 | 5/2001 |
| 6,363,939 B1 | 4/2002 | Wilk | EP | 1 166 721 | 1/2002 |
| 6,375,615 B1 | 4/2002 | Flaherty et al. | GB | 2 316 322 | 2/1998 |
| 6,379,319 B1 | 4/2002 | Garibotto et al. | WO | 98/46119 | 10/1988 |
| 6,387,119 B2 | 5/2002 | Wolf et al. | WO | WO 94/16629 | 8/1994 |
| 6,406,488 B1 | 6/2002 | Tweden et al. | WO | 97/13463 | 4/1997 |
| 6,406,491 B1 | 6/2002 | Vanney | WO | 97/13471 | 4/1997 |
| 6,409,697 B2 | 6/2002 | Eno et al. | WO | WO 97/18768 | 5/1997 |
| 6,409,751 B1 | 6/2002 | Hall et al. | WO | 97/27893 | 8/1997 |
| 6,423,089 B1 | 7/2002 | Gingras et al. | WO | 97/27897 | 8/1997 |
| 6,432,126 B1 | 8/2002 | Gambale et al. | WO | 97/27898 | 8/1997 |
| 6,432,127 B1 | 8/2002 | Kim et al. | WO | 97/32551 | 9/1997 |
| 6,432,132 B1 | 8/2002 | Cottone et al. | WO | WO 97/41916 | 11/1997 |
| 6,447,522 B2 | 9/2002 | Gambale et al. | WO | WO 97/43961 | 11/1997 |
| 6,447,539 B1 | 9/2002 | Nelson et al. | WO | WO 98/02099 | 1/1998 |
| 6,454,760 B2 | 9/2002 | Vanney | WO | 98/06356 | 2/1998 |
| 6,454,794 B1 | 9/2002 | Knudson et al. | WO | 98/08456 | 3/1998 |
| 6,458,323 B1 | 10/2002 | Boeksteggers | WO | 98/10714 | 3/1998 |
| 2001/0004683 A1 | 6/2001 | Gambale et al. | WO | 98/16161 | 4/1998 |
| 2001/0004690 A1 | 6/2001 | Gambale et al. | WO | WO 98/19607 | 5/1998 |
| 2001/0004699 A1 | 6/2001 | Gittings et al. | WO | WO 98/25549 | 6/1998 |
| 2001/0008969 A1 | 7/2001 | Evans et al. | WO | WO 98/44869 | 10/1998 |
| 2001/0012948 A1 | 8/2001 | Vanney | WO | 98/46115 | 10/1998 |
| 2001/0014813 A1 | 8/2001 | Saadat et al. | WO | WO 98/49964 | 11/1998 |
| 2001/0016700 A1 | 8/2001 | Eno et al. | WO | WO 98/53759 | 12/1998 |
| 2001/0025643 A1 | 10/2001 | Foley | WO | WO 98/55027 | 12/1998 |
| 2001/0027287 A1 | 10/2001 | Shmulewitz et al. | WO | WO 98/57591 | 12/1998 |
| 2001/0034547 A1 | 10/2001 | Hall et al. | WO | 99/08624 | 2/1999 |
| 2001/0037117 A1 | 11/2001 | Gambale et al. | WO | 99/17683 | 4/1999 |
| 2001/0037149 A1 | 11/2001 | Wilk | WO | 99/21490 | 5/1999 |
| 2001/0039426 A1 | 11/2001 | Makower et al. | WO | WO 99/21510 | 5/1999 |
| 2001/0039445 A1 | 11/2001 | Hall et al. | WO | WO 99/22655 | 5/1999 |
| 2001/0041902 A1 | 11/2001 | Lepulu et al. | WO | 99/25273 | 5/1999 |
| 2001/0047165 A1 | 11/2001 | Makower et al. | WO | WO 99/32051 | 7/1999 |
| 2001/0053932 A1 | 12/2001 | Phelps et al. | WO | 99/36000 | 7/1999 |
| 2002/0002349 A1 | 1/2002 | Flaherty et al. | WO | 99/36001 | 7/1999 |
| 2002/0004662 A1 | 1/2002 | Wilk | WO | WO 99/37218 | 7/1999 |
| 2002/0004663 A1 | 1/2002 | Gittings et al. | WO | 99/38459 | 8/1999 |
| 2002/0007138 A1 | 1/2002 | Wilk et al. | WO | 99/40868 | 8/1999 |
| 2002/0029079 A1 | 3/2002 | Kim et al. | WO | WO 99/47071 | 9/1999 |
| 2002/0032476 A1 | 3/2002 | Gambale et al. | WO | WO 99/47078 | 9/1999 |
| 2002/0032478 A1 | 3/2002 | Boeksteggers et al. | WO | WO 99/48427 | 9/1999 |
| 2002/0033180 A1 | 3/2002 | Solem | WO | 99/48545 | 9/1999 |
| 2002/0045928 A1 | 4/2002 | Boeksteggers | WO | 99/49793 | 10/1999 |
| 2002/0049486 A1 | 4/2002 | Knudson et al. | WO | 99/49910 | 10/1999 |
| 2002/0058897 A1 | 5/2002 | Renati | WO | 99/51162 | 10/1999 |
| 2002/0062146 A1 | 5/2002 | Makower et al. | WO | 99/53863 | 10/1999 |
| 2002/0065478 A1 | 5/2002 | Knudson et al. | WO | 99/60941 | 12/1999 |
| 2002/0072699 A1 | 6/2002 | Knudson et al. | WO | 99/62430 | 12/1999 |
| 2002/0077566 A1 | 6/2002 | Laroya et al. | WO | 00/09195 | 2/2000 |
| 2002/0092535 A1 | 7/2002 | Wilk | WO | WO 00/10623 | 3/2000 |
| 2002/0095111 A1 | 7/2002 | Tweden et al. | WO | 00/12029 | 3/2000 |
| 2002/0100484 A1 | 8/2002 | Hall et al. | WO | 00/15146 | 3/2000 |
| 2002/0111669 A1 | 8/2002 | Pazienza et al. | WO | 00/15147 | 3/2000 |
| 2002/0111672 A1 | 8/2002 | Kim et al. | WO | 00/15148 | 3/2000 |
| 2002/0116044 A1 | 8/2002 | Cottone, Jr. et al. | WO | 00/15149 | 3/2000 |
| 2002/0123698 A1 | 9/2002 | Garibotto et al. | WO | 00/15275 | 3/2000 |
| 2002/0144696 A1 | 10/2002 | Sharkawy et al. | WO | WO 00/18325 | 4/2000 |
| 2002/0161424 A1 | 10/2002 | Rapacki et al. | WO | WO 00/18326 | 4/2000 |
| 2002/0165479 A1 | 11/2002 | Wilk | WO | 00/21436 | 4/2000 |
| 2002/0165606 A1 | 11/2002 | Wolf et al. | WO | 00/21461 | 4/2000 |
| | | | WO | 00/21463 | 4/2000 |
| | FOREIGN PATENT DOCUMENTS | | WO | WO 00/183331 | 4/2000 |
| EP | 0 876 803 | 11/1998 | WO | 00/24449 | 5/2000 |

| | | |
|---|---|---|
| WO | 00/33725 | 6/2000 |
| WO | WO 00/35376 | 6/2000 |
| WO | WO 00/36997 | 6/2000 |
| WO | 00/41632 | 7/2000 |
| WO | 00/41633 | 7/2000 |
| WO | 00/45711 | 8/2000 |
| WO | WO 00/48530 | 8/2000 |
| WO | 00/56387 | 9/2000 |
| WO | WO 00/56387 | 9/2000 |
| WO | 00/66007 | 11/2000 |
| WO | 00/66009 | 11/2000 |
| WO | 00/66035 | 11/2000 |
| WO | 00/71195 | 11/2000 |
| WO | WO 01/08602 | 2/2001 |
| WO | 01/10340 | 2/2001 |
| WO | 01/10341 | 2/2001 |
| WO | 01/10347 | 2/2001 |
| WO | 01/10348 | 2/2001 |
| WO | 01/10349 | 2/2001 |
| WO | WO 01/10350 A1 | 2/2001 |
| WO | WO 01/17440 A1 | 3/2001 |
| WO | WO 01/26562 | 4/2001 |
| WO | WO 01/49187 A1 | 7/2001 |
| WO | WO 01/54625 | 8/2001 |
| WO | WO 01/70133 | 9/2001 |
| WO | WO 02/02163 | 1/2002 |
| WO | WO 02/02168 | 1/2002 |

OTHER PUBLICATIONS

*The Journal of Thoracic and Cardiovascular Surgery*, "Experimental evaluation of myocardial tunnelization as a method of myocardial revascularization," I. Anabtawi, M.D. et al., pp. 638–646, Nov. 1969.

*American Heart Journal*, "Effects of laser irradiation delivered by flexible fiberoptic system on the left ventricular internal myocardium," G. Lee, M.D. et al., pp. 587–590, vol. 106, No. 3, Sep. 1983.

*Texas Heart Institute Journal*, "Transmyocardial Laser Revascularization," D. A. Cooley, M.D. et al., pp. 220–224, vol. 21, No. 3, 1994.

*American Journal of Physiology*, "Transmural myocardial perfusion during restricted coronary inflow in the awake dog," R. Bache et al., pp. H645–651, vol. 232, No. 6, Jun. 1977.

*The Annals of Thoracic Surgery*, "Myocardial Canalization," A. H. Khazei, M.D. et al., vol. 6, No. 2, Aug. 1968.

*Surgical Forum*, "Proceedings of the 24th Annual Sessions of the Forum on Fundamental Surgical Problems, 54th Clinical Congress of the American College of Surgeons, Chicago, Illinois, Oct., 1968," pp. 156–159, American College of Surgeons, Chicago, Illinois.

Tweden et al, "Ventriculocoronary Artery Bypass (VCAB), a Novel Approach to Myocardial Revascularization" 2/2000.

Gardner, M.D. et al., "An Experimental Anatomic Study of Indirect Myocardial Revascularization," *Journal of Surgical Research*, May 1971, vol. 11, No. 5, pp. 243–247.

Palmaz et al., "Expandable Intrahepatic Portacaval Shunt Stents: Early Experience in the Dog," *AJR*, 1985, vol. 145, pp. 821–825.

Palmaz et al., "Expandable Intrahepatic Portacaval Shunt Stents in Dogs with Chronic Portal Hypertension," *AJR*, 1986, vol. 147, pp. 1251–1254.

Richter, M.D. et al., "Transjugular Intrahepatic Portacaval Stent Shunt: Preliminary Clinical Results," *Radiology*, 1990, vol. 174, No. 3, pp. 1027–1030.

Zemel, M.D. et al., "Percutaneous Transjugular Portosystemic Shunt," *JAMA*, vol. 266, No. 3, pp. 390–393.

Massimo, M.D. et al., "Myocardial Revascularization by a New Method of Carrying Blood Directly from the Left Ventricular Cavity into the Coronary Circulation," *Journal of Thoracic Sueons*, Aug. 1997, vol. 34, No. 2, pp. 257–264.

Lary, M.D. et al., "Myocardial Revascularization Experiments Using the Epicardium," *Archives of Surgery*, Jan. 1969, vol. 98, No. 1, pp. 69–72.

Munro, M.D. et al., "The possibility of myocardial revascularization by creation of a left ventriculocoronary artery fistula," *Journal of Thoracic and Cardiovascular Surgery*, Jul. 1969, vol. 58, No. 1, pp. 25–32.

Kuzela, M.D. et al., "Experimental evaluation to direct transventricular revascularization," *The Journal of Thoracic and Cardiovascular Surgery*, Jun. 1969, vol 57, No. 6, pp. 770–773.

* cited by examiner

US 6,641,610 B2

VALVE DESIGNS FOR LEFT VENTRICULAR CONDUITS

CROSS-REFERENCE TO RELATED APPLICATION

This application claims the benefit of U.S. Provisional Application Ser. No. 60/099,777, filed Sep. 10, 1998.

FIELD OF THE INVENTION

This invention relates to apparatus and method for implanting a conduit to allow communication of fluids from one portion of a patient's body to another; and, more particularly, to a blood flow conduit to allow communication from a heart chamber to a vessel or vice versa, and/or vessel to vessel. Even more particularly, the invention relates to a left ventricular conduit and related conduit configurations for controlling the flow of blood through the conduit to achieve bypass of a stenosed or occluded coronary artery.

BACKGROUND OF THE INVENTION

Coronary artery disease is a major problem in the U.S. and throughout the world. Coronary arteries as well as other blood vessels frequently become clogged with plaque, which at the very least impairs the efficiency of the heart's pumping action, and can lead to heart attack, arrhythmias, and death. In some cases, these arteries can be unblocked through noninvasive techniques such as balloon angioplasty. In more difficult cases, a bypass of the blocked vessel is necessary.

In a bypass operation, one or more venous segments are inserted between the aorta and the coronary artery. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass surgery, however, is a very intrusive procedure that is expensive, time-consuming and traumatic to the patient. The operation requires an incision through the patient's sternum (sternotomy), and that the patient be placed on a bypass pump so that the heart can be operated on while not beating. A vein graft is harvested from the patient's leg, and a delicate surgical procedure is required to piece the bypass graft to the coronary artery (anastomosis). Hospital stays subsequent to the surgery and convalescence are prolonged. Furthermore, many patients are poor surgical candidates due to other concomitant illnesses.

As mentioned above, another conventional treatment is percutaneous transluminal coronary angioplasty (PTCA) or other types of angioplasty. However, such vascular treatments are not always indicated due to the type of location of the blockage or stenosis, or due to the risk of emboli.

Thus, there is a need for an improved bypass system that is less traumatic to the patient.

SUMMARY OF THE INVENTION

The preferred embodiments of the present invention address the need in the previous technology by providing a bypass system that avoids the sternotomy and other intrusive procedures normally associated with coronary bypass surgery. These embodiments also free the surgeon from the need to perform multiple anastomoses as is necessary in the current process.

The preferred device provides a conduit or shunt for diverting blood directly from the left ventricle of the heart to a coronary artery, at a point distal to the blockage or stenosis, thereby bypassing the blocked portion of the vessel. The conduit preferably comprises a tube adapted to be positioned in the myocardium and having a one way valve therein. The valve prevents the backflow of blood from the coronary artery into the left ventricle.

The conduit device is delivered through the coronary artery to a position distal the blockage or stenosis. At that position, the coronary artery, the myocardium and the wall of the left ventricle are pierced to provide an opening or channel completely through from the coronary artery to the left ventricle of the heart. The conduit is then positioned in the opening to provide a permanent passage for blood to flow between the left ventricle of the heart and the coronary artery, distal to the blockage or stenosis. The conduit is sized so that one open end is positioned within the coronary artery, while the other open end is positioned in the left ventricle. The hollow lumen of the conduit provides a passage for the flow of blood.

To prevent the backflow of blood from the coronary artery to the left ventricle of the heart, the conduit is provided with a one-way valve. The valve is preferably a windsock type valve, a flapper valve, a bi- or tricuspid valve, a ball valve, a valve formed from the myocardium itself, or a valve that opens and closes in response to the contraction and relaxation of the heart muscle, or in response to the electrical signals in the heart.

DETAILED DESCRIPTION OF THE PREFERRED EMBODIMENT

Figure 1A:
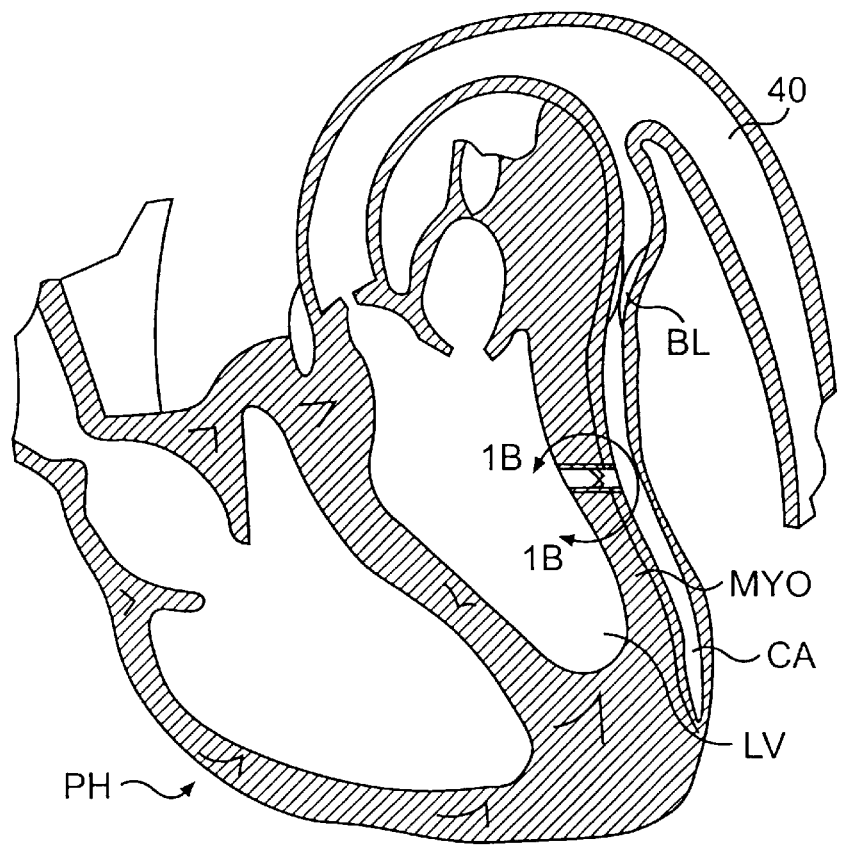
FIG. 1A is a schematic, cross-sectional view of a human heart, showing a conduit in the myocardium of the heart for forming a bypass between the left ventricle and a coronary artery.

As is well known, the coronary artery branches off the aorta and is positioned along the external surface of the heart wall. Oxygenated blood that has returned from the lungs to the heart then flows from the heart to the aorta. Some blood in the aorta flows into the coronary arteries, and the remainder of blood in the aorta flows on to the remainder of the body. The coronary arteries are the primary blood supply to the heart muscle and are thus critical to life. In some individuals, atherosclerotic plaque, aggregated platelets, and/or thrombi build up within the coronary artery, blocking the free flow of blood and causing complications ranging from mild angina to heart attack and death. The presence of coronary vasospasm, also known as "variant angina" or "Prinzmetal's angina," compounds this problem in many patients.

As used herein, the term "heart chamber" primarily refers to the interior, or lumenal, aspect of the left or right ventricle or the left or right atrium. The term "conduit," "stent," and "tube" herein refer to physical structures, preferably primarily artificial, that can be positioned between two or more chambers or vessels, to allow blood flow from one chamber or vessel to another. A "shunt" is any natural or artificial passage between natural channels, such as heart chambers or blood vessels. The conduit in the preferred arrangement can be made of a variety of materials, including various metals, such as nitinol, or plastics.

As used herein, the term "heart wall" comprises any one or more of the following portions or layers of the mammalian heart: the epicardium, myocardium, endocardium, pericardium, interatrial septum, and interventricular septum.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other nonmyocardial and even noncardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the obstructions that are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods are disclosed. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

In order to restore the flow of oxygenated blood through the coronary artery, the preferred arrangement provides for the shunting of blood directly from the heart to a site in the coronary artery which is distal the blockage or stenosis.

Although the specification herein will describe the conduit primarily with reference to the left ventricle, the preferred arrangement can be used with any of the four heart chambers, and with any coronary artery, including the left main coronary artery, the right coronary artery, the left anterior descending artery, the left circumflex artery, the posterior descending artery, the obtuse marginal branch or a diagonal branch.

A tunnel or opening is formed through the wall of the coronary artery and the heart wall and into the left ventricle of the heart which lies beneath, or deep to, the coronary artery. A conduit is positioned in the opening to keep it open, and a one-way valve is positioned within the conduit to prevent blood from flowing back into the left ventricle of the heart from the coronary artery.

The conduit may be introduced into the heart wall in a variety of ways, including by a catheter threaded through the femoral artery into the aorta and thence into the left ventricle and, if necessary, the left atrium; or by a catheter threaded through the femoral vein into the inferior vena cava and thence into the right atrium and right ventricle. Alternatively, the conduit may be introduced through a surgical incision in chest wall (thoracotomy) or sternum (sternotomy).

Further details regarding conduits and conduit delivery systems are described in U.S. patent applications entitled DELIVERY METHODS FOR LEFT VENTRICULAR CONDUIT, U.S. application Ser. No. 09/368,868, now U.S. Pat. No. 6,261,304; DESIGNS FOR LEFT VENTRICULAR CONDUIT, U.S. application Ser. No. 09/369,048, now U.S. Pat. No. 6,290,728; LEFT VENTRICULAR CONDUIT WITH BLOOD VESSEL GRAFT, U.S. application Ser. No. 09/369,061, now U.S. Pat. No. 6,254,564; LEFT VENTRICULAR CONDUITS TO CORONARY ARTERIES AND METHODS FOR CORONARY BYPASS, U.S. application Ser. No. 09/369,039, now abandoned; and BLOOD FLOW CONDUIT DELIVERY SYSTEM AND METHOD OF USE, U.S. application Ser. No. 09/368,644, now U.S. Pat. No. 6,302,892, filed on the same day as the present application, and U.S. Pat. Nos. 5,429,144, and 5,662,124, the disclosures of which are all hereby incorporated by reference in their entirety.

The opening through the heart wall (including endocardium, myocardium, and epicardium) and coronary artery can be formed in a variety of ways, including by knife or scalpel, electrocautery, cryoablation, radiofrequency ablation, ultrasonic ablation, and the like. Other methods will be apparent to those of ordinary skill in the art.

Figure 1B:
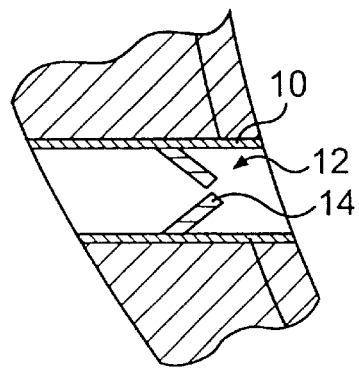
FIG. 1B is an enlarged view of the bypass conduit of FIG. 1A.

Referring now to FIGS. 1A and 1B, a coronary artery bypass is accomplished by disposing a conduit 12 (FIG. 1B) in a heart wall or myocardium MYO of a patient's heart PH (FIG. 1A). The conduit 12 preferably extends from the left ventricle LV of heart PH to a clogged coronary artery CA at a point downstream of a blockage BL to create a passageway therethrough. Conduit 12 is preferably made of a biocompatible material such as stainless steel or nitinol, although other materials such as Ti, Ti alloys, Ni alloys, Co alloys and biocompatible may also be used. In one embodiment, conduit 12 has a one way valve 14 to allow blood to flow from the left ventricle LV to the coronary artery CA. Although the conduit 12 may elastically deform under the contractive pressure of the heart muscle during systole, the stent remains open to allow blood to pass from the patient's left ventricle LV into the coronary artery CA. During diastole, the blood pumped into coronary artery through passageway is blocked by one-way valve 14 from returning to left ventricle LV.

Figure 2:
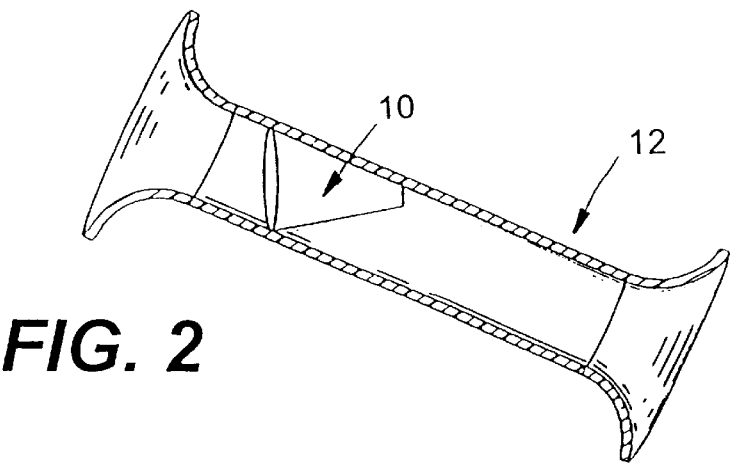
FIG. 2 is a cross-sectional view of a windsock valve incorporated into a heart conduit in accordance with a preferred arrangement.

One embodiment of the preferred arrangement is illustrated in FIG. 2. The valve 10 incorporates a design similar to a windsock. The valve 10 is preferably formed from a biocompatible fabric-like material incorporated during the construction of the conduit 12. The high-pressure blood flow causes the valve 10 to open, while the backflow of blood catches the edges of the valve 10 and causes it to close, stopping the flow. The valve 10 can be positioned anywhere along the length of the conduit 12.

The valve 10 is preferably constructed from a biocompatible and very compliant fabric or other material that is pushed aside by the high forward blood pressure created from the contraction of the heart muscle, but opens to "catch" the back-flow of blood passing back through the conduit 12. The valve 10 is preferably constructed by incorporating the fabric or other material into the conduit 12 directly during its manufacture. This allows the valve 10 and conduit 12 to be introduced as a single unit.

Figure 3:
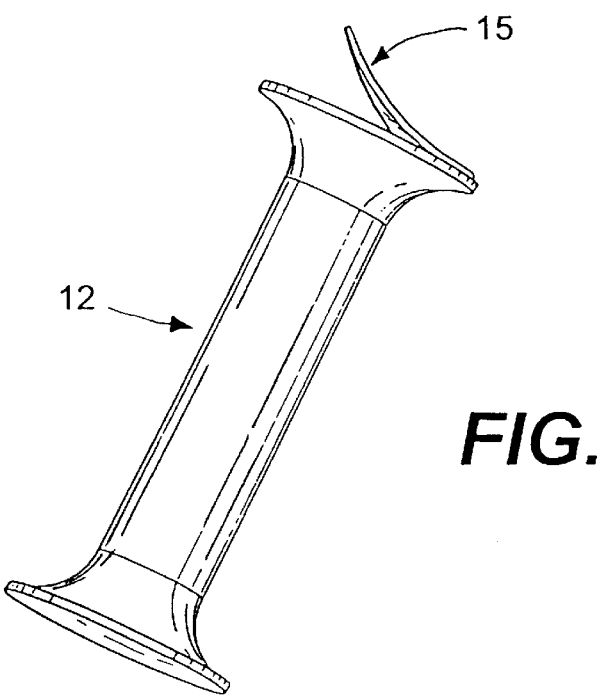
FIG. 3 is a perspective view of a flapper valve incorporated into a heart conduit in accordance with a preferred arrangement.

Another embodiment of the preferred arrangement is illustrated in FIG. 3. This valve 15 is a type of "flapper valve" that is built onto the end of the conduit 12 that is positioned in the coronary artery. The high-pressure blood flow opens the flap 15 and the backflow of blood causes the flap 15 to shut. This flap 15 is slightly larger than the conduit 12 inner diameter (D) to accomplish this action and to ensure a proper seal. The valve 15 is preferably formed from the same material as the conduit 12 and the two are preferably introduced as a single unit. Alternatively, the valve 15 may be attached as a secondary operation once the conduit 12 is in place.

Figure 4:
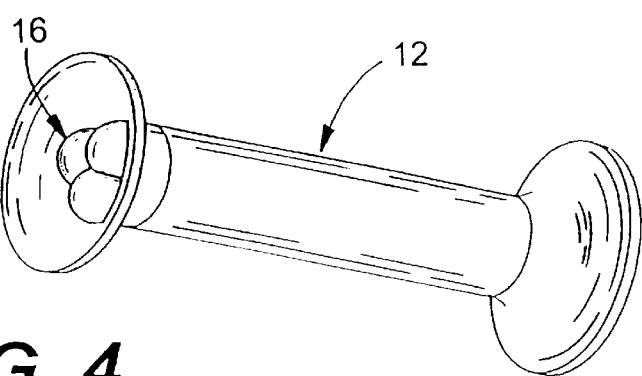
FIG. 4 is a perspective view of a tricuspid valve incorporated into a heart conduit in accordance with the preferred arrangement.

The third embodiment of the valve 16 is illustrated in FIG. 4. This valve 16 is similar to a natural heart valve. A bi- or tricuspid arrangement of semi-circular spheres is forced open by the high-pressure flow and collapses back to prevent back-flow of blood through the conduit 12. This valve 16 is preferably made from the same material as the conduit 12, or alternatively, from a thin biocompatible material that is built onto the conduit 12. Preferably, the valve 16 and the conduit 12 are manufactured together and introduced as a single unit. Alternatively, the valve 16 may be attached to the conduit 12 in a secondary operation once the conduit 12 is in place. The valve 16 may be placed at any location along the length of the conduit 12.

Figure 5A:
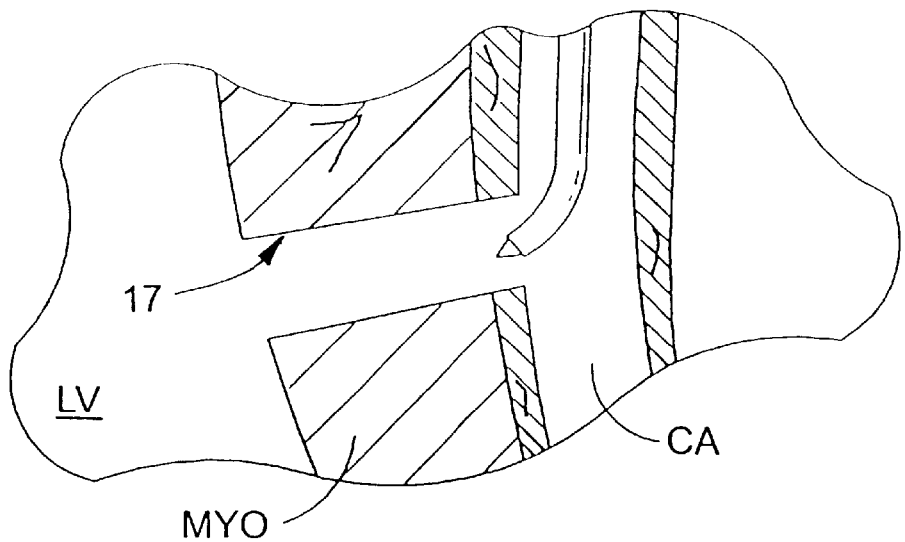
FIGS. 5A–D are cross-sectional views of a valve formed from the myocardium for use in conjunction with a heart conduit in accordance with a preferred arrangement.
Figure 5B:
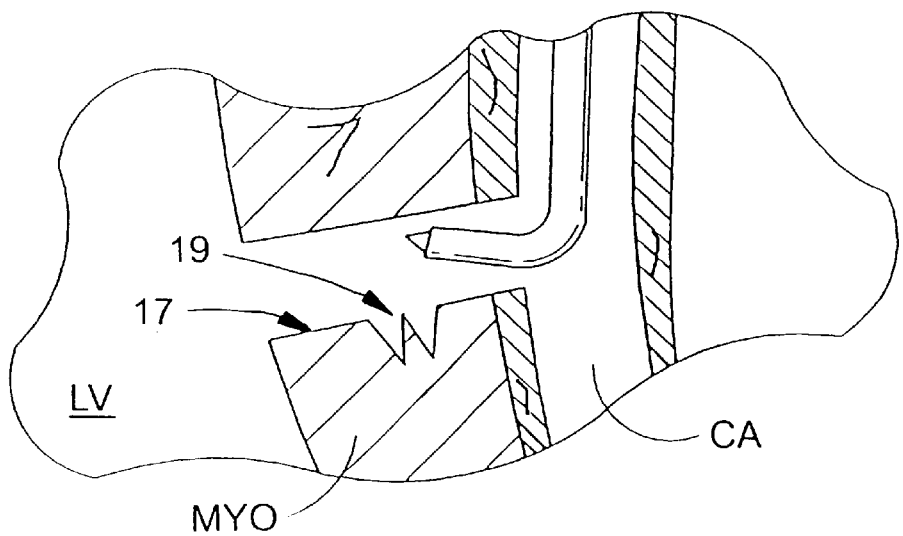

A further embodiment of the conduit is illustrated in FIGS. 5A–D. Here, the heart wall, which includes the myocardium MYO, lying between the coronary artery CA and the left ventricle of the heart LV, is cut using known techniques to form a passage through the myocardium MYO. FIG. 5A shows the myocardium MYO after a cut or puncture has been made in it, with a free edge 17 shown at each margin of the cut or puncture. FIG. 5B shows the myocardium MYO after a jagged or irregular surface 19 has been made with a cutting tool in the free edge 17 of the myocardium MYO. Such cutting tools may include knives, scalpels, lasers, radiofrequency probes, and other cutting tools known to those of skill in the art.

Figure 5C:
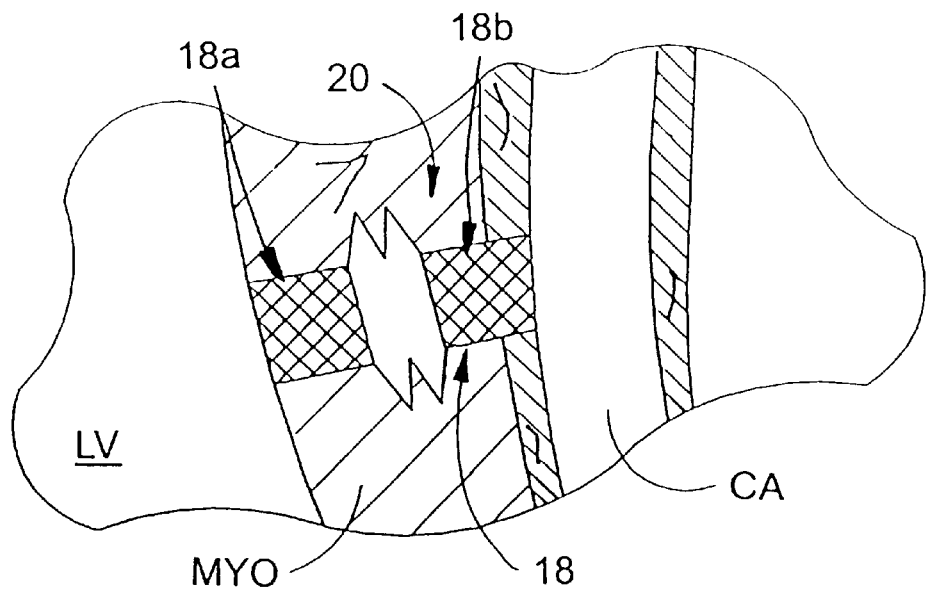
Figure 5D:
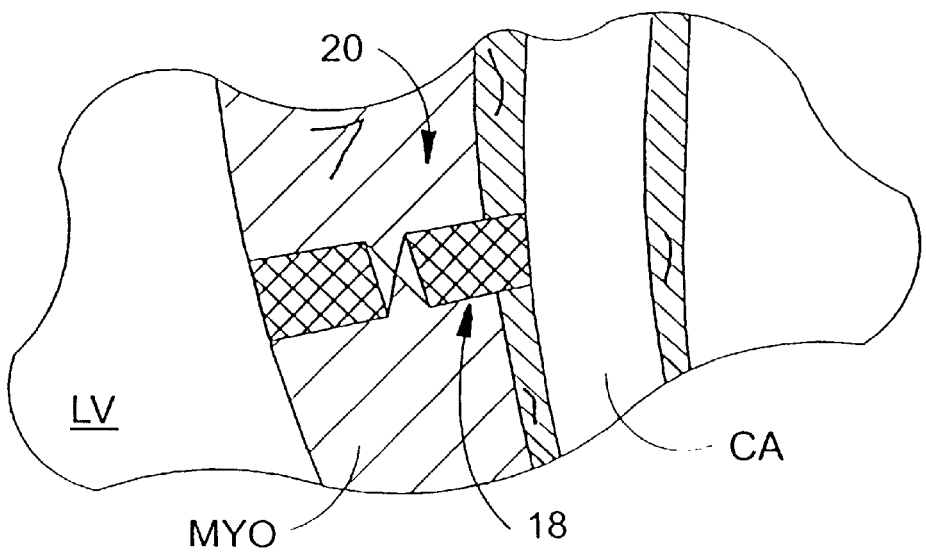

As illustrated in FIG. 5C, two conduits, an upper or lower conduit, or a single conduit 18 having upper 18a and lower 18b components, is positioned in the passage. The myocardium MYO is left free between the two edges of the conduit 18 to form the valve 20. FIG. 5D shows that during diastole, the edges or free portions of the myocardium MYO come together, closing the passage through the myocardium MYO. During systole, the free portions of the myocardium MYO can move away from one another as cardiac myofibrils contract, opening the passage through the myocardium MYO, as illustrated in FIG. 5C. Thus, the heart muscle MYO itself can form at least part of the valve 20 in the conduit 18 to prevent the backflow of blood.

Figure 6A:
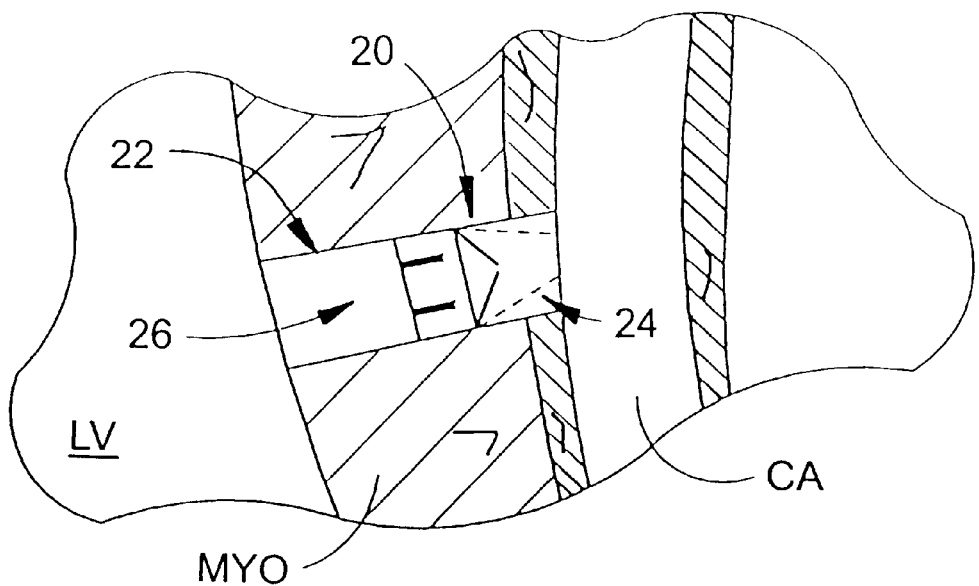
FIGS. 6A–B are cross-sectional views of a valve that is activated by the contractions of the heart muscle for use in conjunction with a heart conduit in accordance with a preferred arrangement.
Figure 6B:
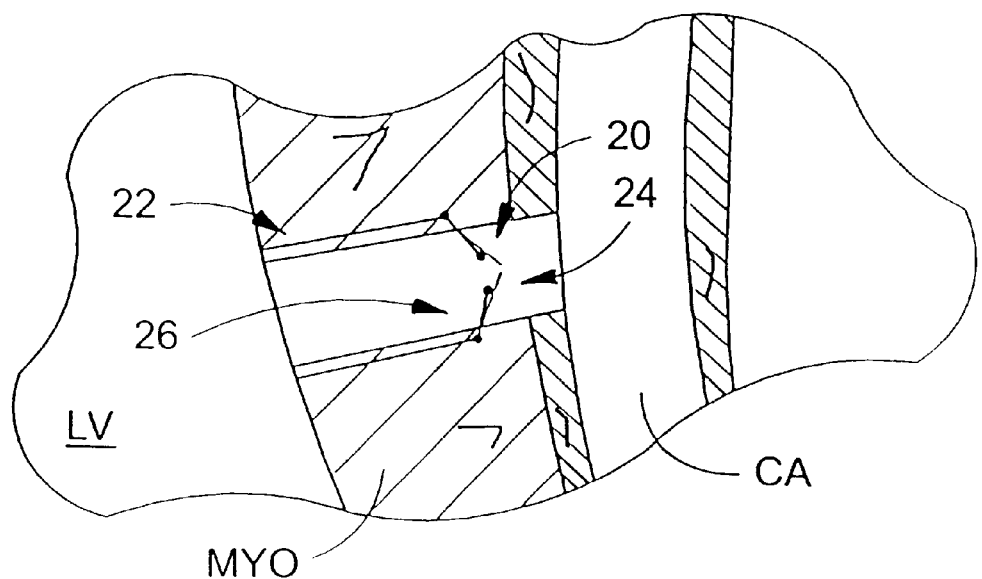

In another embodiment, the valve in the conduit may be controlled in response to the contractions of the heart. As illustrated in FIGS. 6A and 6B, two conduits (FIG. 6A), an upper conduit 20 and lower conduit 22, or a single conduit (FIG. 6B) having upper moveable components 20 and lower moveable components 22, are positioned in the passage in the myocardium MYO between the left ventricle LV and the coronary artery CA. The conduit or conduits contain a valve 24, which is normally in a closed position, and an actuator 26, which is adapted to open the valve 24 in the conduit. During diastole, when the heart muscle MYO is relaxed, the two conduits or the two components of the conduit 20, 22 are positioned such that the valve 24 remains closed. During systole, the two conduits or components 20, 22 are brought close together, such that the actuator 26 forces the valve 24 to open and allows for the passage of blood therethrough.

Thus, the contractions of the heart muscle MYO control the valve 24 in the conduit to prevent the backflow of blood during part of the cardiac cycle, for example diastole.

The valve 24 may also be controlled by a hydrodynamic or electric pump or motor, which is reponsive to the contractions of the heart, causing the valve 24 to open and close in response to various parts of the cardiac cycle.

Figure 7:
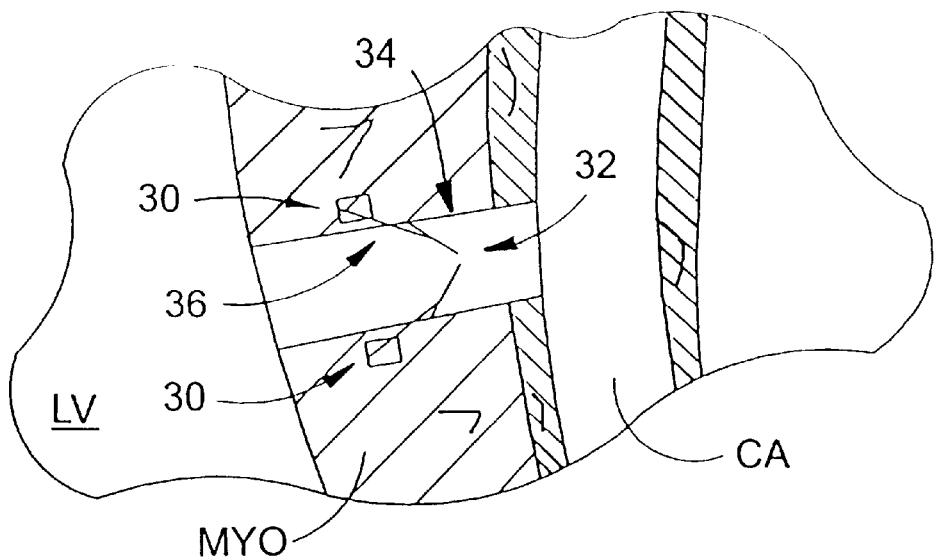
FIG. 7 is a cross-sectional view of a valve that is activated by the electrical signals in the heart muscle for use in conjunction with a heart conduit in accordance with a preferred arrangement.

A further embodiment of the preferred arrangement is illustrated in FIG. 7. In this embodiment, electrical sensors 30 regulate the opening and closing of the valve 32 positioned within the conduit 34. The sensor 30 senses the electrical signals produced in the heart muscle, and causes the valve 32 to open during systole, and to close during diastole. This is accomplished by having an actuator 36 act in response to the electrical signals detected by the sensor 30, to open and close the valve 32. For example, the valve 32 can be biased in a closed position. When the sensor 30 detects the electrical signal that occurs during or immediately precedes systole, e.g., a QRS complex in the electrocardiogram, the sensor 30 signals the actuator 36 to force open the valve 32 and allow for the flow of blood therethrough. During diastole, the sensor 30 signals the actuator 36 to allow the valve 32 to close and prevent any backflow of blood. Alternatively, the valve 32 can be biased in an open position. When the sensor 30 senses diastole, such as through coordination with the P wave or PR interval in the electrocardiogram, or, for example, after the sensor delays for a predetermined time period after the QRS complex occurs in the electrocardiogram, it signals the actuator 36 to close the valve 32 and prevent the backflow of blood.

Figure 8:
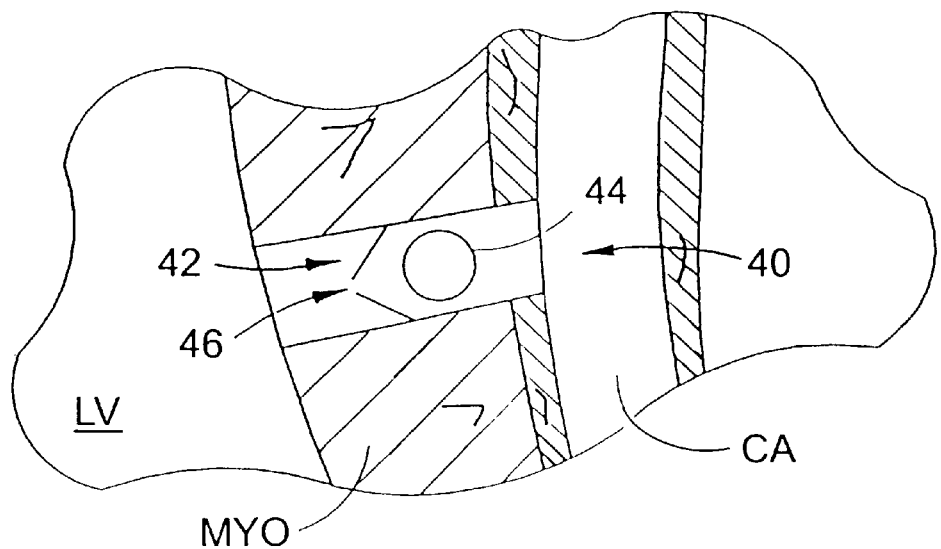
FIG. 8 is a cross-sectional view of a ball valve incorporated into a heart conduit in accordance with a preferred arrangement.

Another embodiment is illustrated in FIG. 8. This valve 42 is a type of "ball valve" that is built into the conduit 40 that is positioned in the coronary artery. The high-pressure blood flow from the left ventricle LV to the coronary artery CA opens the valve 42 by moving the ball 44 away from the opening 46. The backflow of blood from the coronary artery CA to the left ventricle LV causes the ball 44 to seat against the opening 46, thereby closing the valve 42 and preventing the backflow of blood. The valve 42 and the conduit 40 are preferably introduced as a single unit.

Figure 9A:
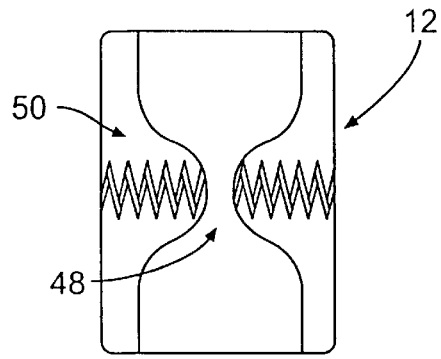
FIGS. 9A–9B are cross-sectional views of a valve with spring mechanisms incorporated into a heart conduit.
Figure 9B:
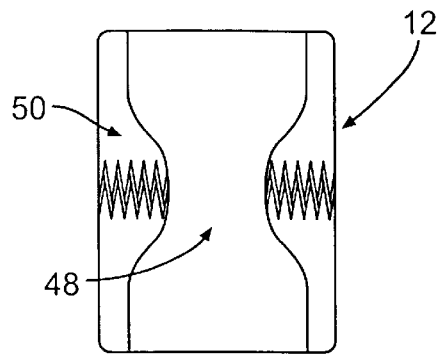

Another embodiment is illustrated in FIGS. 9A and 9B. The conduit 12 has a valve 48 with one or more spring mechanisms 50 within its walls. In diastole (FIG. 9A), bloodflow pressure through the valve is relatively low, and the valve assumes a relatively closed position, impeding the passage of blood through the valve 48. In systole (FIG. 9B), flow pressure through the valve is relatively high, and the valve 48 opens as the spring mechanism 50 contracts, to allow blood to flow through the valve 48.

Figure 9C:
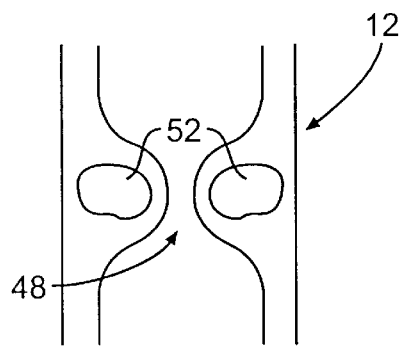
FIGS. 9C–9D are cross-sectional views of a valve with a balloon mechanism incorporated into a heart conduit.
Figure 9D:
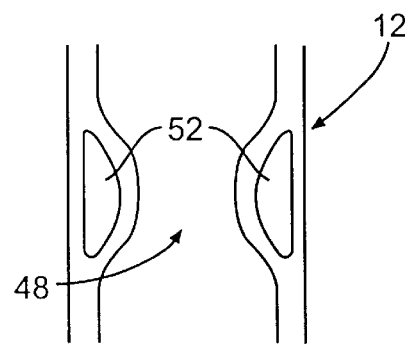
Figure 9E:
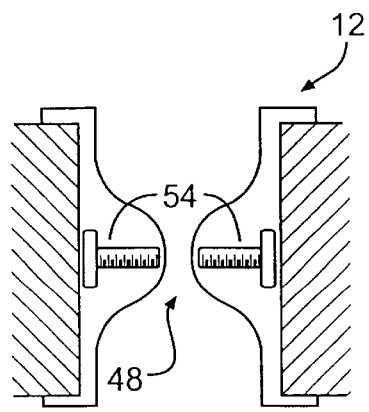
FIGS. 9E–9F are cross-sectional views of a valve with an internal motor incorporated into a heart conduit.
Figure 9F:
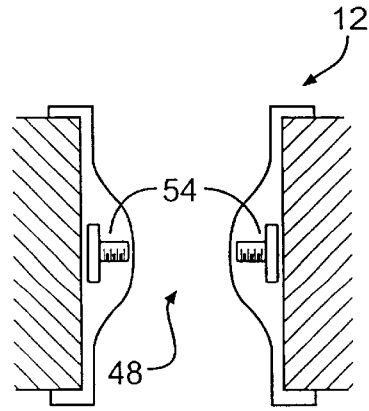

Instead of a spring mechanism 50, the walls of the conduit 12 can have other mechanisms therein to allow differential flow during various parts of the cardiac cycle. For example, the valve 48 can have a gas- or liquid-filled balloon 52 in its wall, as shown in FIGS. 9C and 9D. This balloon mechanism can contract (FIG. 9D, during systole) or expand (FIG. 9C, during diastole) in response to fluid pressure, to allow the valve 48 to open and close, respectively. Alternatively, the valve 48 can have an internal motor 54, shown in FIGS. 9E and 9F, that opens and closes the valve 48 in response to electrical or mechanical signals from the heart during various parts of the cardiac cycle. For example, as illustrated in FIG. 9E, during diastole, the motor preferably closes the valve 48, and during systole, the motor preferably opens the valve 48.

Figure 10A:
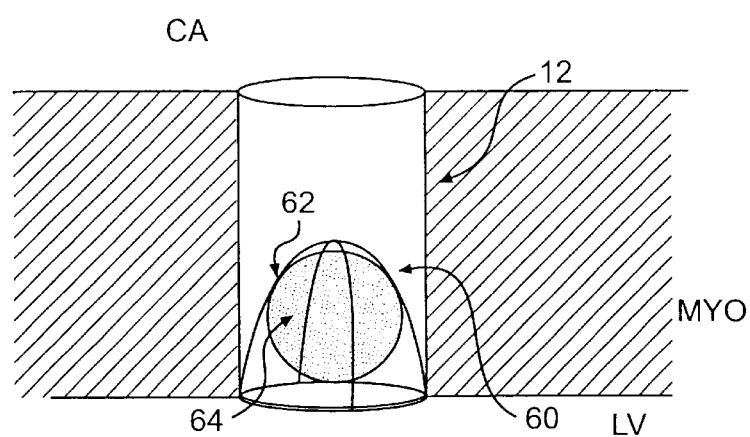
FIG. 10A is a partial cross-sectional view of a ball and cage valve incorporated into a heart conduit.

Another embodiment of the valve mechanism is illustrated in FIG. 10A. The conduit 12 has a ball valve 60 that is of the ball-and-cage variety, for example, like the Starr-Edwards heart valve known to those of skill in the art. This valve 60 typically has a wire or mesh cage 62 with a ball 64 within it. The conduit is positioned within the myocardium MYO. During blood flow from the left ventricle LV to the coronary artery CA, the ball 64 moves toward the apex of the cage 62, permitting blood to flow around the ball 64 and through the conduit 12. During backflow of blood from the coronary artery CA to the left ventricle LV, the ball 64 moves toward the base of the cage 62 and seats thereon, fitting tightly onto the base of the cage 62, and blocking the flow of blood from the coronary artery CA to the left ventricle LV.

Figure 10B:
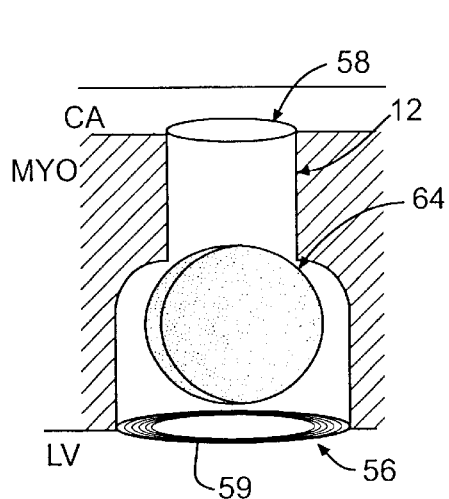
FIG. 10B is a cross-sectional view of a ball valve incorporated into a heart conduit having a narrower distal end.
Figure 10C:
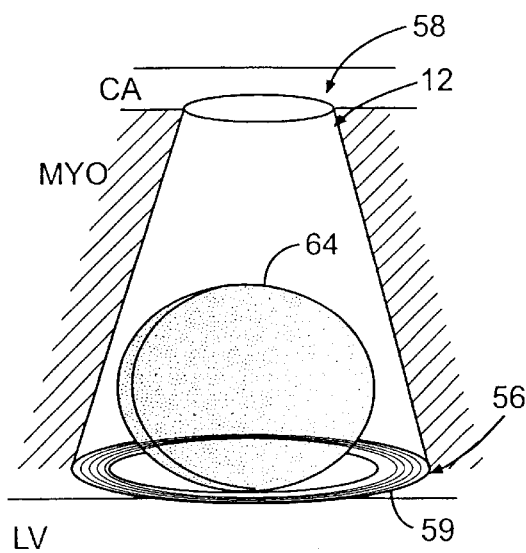
FIG. 10C is a cross-sectional view of a ball valve incorporated into a heart conduit having a smooth taper.

FIG. 10B illustrates another embodiment wherein a ball 64 is provided within a conduit 12 that is wider at proximal end 56 facing the left ventricle, and narrower at distal end 58 facing the coronary artery. FIG. 10C illustrates a similar embodiment wherein the conduit 12 has a gradual taper from the proximal end 56 to distal end 58. Like the embodiment of FIG. 10A, during blood flow from the proximal end 56 to distal end 58, the ball 64 moves toward the coronary artery CA to allow blood flow around the ball through the conduit. In one embodiment, the cross-section of the conduit 12 in FIGS. 10B and 10C is noncircular, for example elliptical, to allow blood to flow around the ball 64. During backflow from the coronary artery CA to the left ventricle LV, the ball moves against the base 59 of the conduit to block flow of blood therethrough.

The present vascular conduit and valve system provides significant improvements in the present treatment of blockages and significant stenoses in the coronary artery. Although the invention has been described in its preferred embodiments in connection with the particular figures, it is not intended that this description should be limited in any way.

What is claimed is:

1. A device for treating a heart, the device comprising:
   at least one hollow implant defining a lumen, the at least one hollow implant being configured to be positioned in a heart wall between a heart chamber and a coronary vessel,
   wherein, when the at least one hollow implant is positioned in the heart wall, the lumen at least partially defines a blood flow passage between the heart chamber and the coronary vessel, and
   wherein the passage is at least partially closable in response to movement of cardiac tissue during diastole so as to at least partially obstruct blood flow therethrough.

2. The device of claim 1, wherein the lumen is configured so that, when the at least one hollow implant is positioned in the heart wall, the lumen is open to permit blood flow through the passage during systole.

3. The device of claim 1, wherein the at least one hollow implant includes a hollow tube.

4. The device of claim 1, wherein the at least one hollow implant includes a conduit.

5. The device of claim 1, wherein the at least one hollow implant includes a stent.

6. The device of claim 1, wherein the at least one hollow implant includes two hollow implants.

7. The device of claim 6, wherein the hollow implants are configured to be separated from each other when the hollow implants are positioned in the heart wall.

8. The device of claim 6, wherein a length of each hollow implant is less than a thickness of the heart wall.

9. The device of claim 1, wherein the at least one hollow implant is configured to be positioned in the heart wall between a left ventricle and a blood vessel.

10. The device of claim 1, wherein the at least one hollow implant is configured to be positioned in the heart wall between the heart chamber and a coronary artery.

11. The device of claim 1, wherein the at least one hollow implant is configured to be positioned in the heart wall between a left ventricle and a coronary artery.

12. The device of claim 11, wherein the passage is configured to permit blood to flow from the left ventricle to the coronary artery when blood flow through the passage is not partially obstructed.

13. The device of claim 1, wherein the passage is closable such that blood flow through the passage is fully obstructed in response to movement of the cardiac tissue during diastole.

14. The device of claim 1, wherein the cardiac tissue includes the heart wall.

15. A device for treating a heart, the device comprising:
at least one hollow implant defining a lumen, the at least one implant being configured to be positioned in a heart wall between a heart chamber and a coronary vessel,
wherein, when the at least one hollow implant is positioned in the heart wall, the lumen at least partially defines a blood flow passage between the heart chamber and the coronary vessel, and
wherein the passage is at least partially closable by cardiac tissue entering the passage so as to at least partially obstruct blood flow therethrough during at least a portion of a cardiac cycle.

16. The device of claim 15, wherein the lumen is configured so that, when the at least one hollow implant is positioned in the heart wall, the lumen is open to permit blood flow through the passage during systole.

17. The device of claim 15, wherein the at least one hollow implant includes a hollow tube.

18. The device of claim 15, wherein the at least one hollow implant includes a conduit.

19. The device of claim 15, wherein the at least one hollow implant includes a stent.

20. The device of claim 15, wherein the at least one hollow implant includes two hollow implants.

21. The device of claim 20, wherein the hollow implants are configured to be separated from each other when the hollow implants are positioned in the heart wall.

22. The device of claim 21, wherein a length of each hollow implant is less than a thickness of the heart wall.

23. The device of claim 15, wherein the at least one hollow implant is configured to be positioned in the heart wall between a left ventricle and a blood vessel.

24. The device of claim 15, wherein the at least one hollow implant is configured to be positioned in the heart wall between the heart chamber and a coronary artery.

25. The device of claim 15, wherein the at least one hollow implant is configured to be positioned in the heart wall between a left ventricle and a coronary artery.

26. The device of claim 25, wherein the passage is configured to permit blood to flow from the left ventricle to the coronary artery when blood flow through the passage is not partially obstructed.

27. The device of claim 15, wherein, when the at least one hollow implant is positioned in the heart wall, the passage is closable by the cardiac tissue so as to fully obstruct the blood flow therethrough during at least a portion of the cardiac cycle.

28. The device of claim 15, wherein the cardiac tissue includes the heart wall.

29. The device of claim 28, wherein, when the at least one hollow implant is positioned in the heart wall, the passage is at least partially closable by portions of the heart wall coming together so as to at least partially obstruct blood flow therethrough during at least a portion of the cardiac cycle.

30. The device of claim 15, wherein, when the at least one hollow implant is positioned in the heart wall, the passage is at least partially closable by the cardiac tissue so as to at least partially obstruct blood flow therethrough during diastole.

31. The device of claim 1, wherein the cardiac tissue is myocardial tissue.

32. The device of claim 15, wherein the cardiac tissue is myocardial tissue.

* * * * *

UNITED STATES PATENT AND TRADEMARK OFFICE
CERTIFICATE OF CORRECTION

PATENT NO. : 6,641,610 B2
DATED : November 4, 2003
INVENTOR(S) : Scott J. Wolf et al.

It is certified that error appears in the above-identified patent and that said Letters Patent is hereby corrected as shown below:

Title page,
Item [75], Inventors, please delete "Scott J. Wolf, Minneapolis, MN (US); Greg R. Furnish, Louisville, KY (US); and David Y. Phelps, Louisville KY (US);" please replace "Nancy C. Briefs" with -- Nancy M. Briefs -- and after "Nashua, NH (US)" delete ";"; and please delete "William Santamore, Medford, NJ (US); Daniel Burkhoff, Tenafly, NJ (US)".

Signed and Sealed this

Twentieth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,641,610 B2
DATED : November 4, 2003
INVENTOR(S) : Scott J. Wolf et al.

It is certified that error appears in the above-identified patent and that said Letters Patent is hereby corrected as shown below:

Title page,
Item [75], Inventors, should read:
-- Scott J. Wolf, Minneapolis, MN; Peter J. Wilk, New York, NY; Nancy M. Briefs Nashua, NH --.

This certificate supersedes Certificate of Correction issued July 20, 2004.

Signed and Sealed this

Third Day of May, 2005

JON W. DUDAS
*Director of the United States Patent and Trademark Office*